US012317386B2

(12) United States Patent
Maa et al.

(10) Patent No.: US 12,317,386 B2
(45) Date of Patent: May 27, 2025

(54) LIGHTING APPARATUS WITH INVISIBLE STROBING

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 280 days.

(21) Appl. No.: 18/198,052

(22) Filed: May 16, 2023

(65) Prior Publication Data

US 2023/0292417 A1 Sep. 14, 2023

Related U.S. Application Data

(63) Continuation-in-part of application No. 18/101,569, filed on Jan. 25, 2023, now Pat. No. 12,127,314, (Continued)

(51) Int. Cl.
*H05B 45/305* (2020.01)
*A61N 5/06* (2006.01)
(Continued)

(52) U.S. Cl.
CPC .......... *H05B 45/305* (2020.01); *H05B 45/10* (2020.01); *H05B 45/20* (2020.01); *A61N 5/0618* (2013.01)

(58) Field of Classification Search
CPC ...... H05B 45/20; H05B 47/155; H05B 45/10; H05B 45/305; F21Y 2115/10; F21S 41/141; G09G 2320/0666; A61B 5/165; A61B 5/4815; A61B 5/0205; A61B 5/024; A61B 5/4812; A61B 5/0031; A61B 5/021; A61B 5/11; A61B 5/1103; A61B 5/1106; A61B 5/1113; A61B 5/4064; A61B 5/4088; A61B 5/4809; A61B 5/4818; A61B 5/4821; A61B 5/4836; A61B 5/4884; A61B 2560/0247; A61B 5/0022; A61B 5/0077; A61B 5/01; A61B 5/02055; A61B 5/02438; A61B 5/0531; A61B 5/0816; A61B 5/1114; A61B 5/1118; A61B 5/14532; A61B 5/14551; A61B 5/162; A61B 5/163; A61B 5/168;
(Continued)

(56) References Cited

U.S. PATENT DOCUMENTS

| | | | | |
|---|---|---|---|---|
| 2015/0173147 A1* | 6/2015 | Casper | ................ | H05B 47/196 315/152 |
| 2020/0359479 A1* | 11/2020 | Le Floch | ................ | F21S 6/003 |
| 2022/0036793 A1* | 2/2022 | Petluri | .................... | G09G 3/32 |

* cited by examiner

*Primary Examiner* — Monica C King
(74) *Attorney, Agent, or Firm* — Andy M. Han; Han IP PLLC

(57) ABSTRACT

A lighting apparatus includes a light source and a controller. The controller turns on the light source with a strobing frequency between 35 Hz and 45 Hz. Moreover, the controller regulates the light output of the light source with a modulation depth percentage less than 50%. The modulation depth may be adjustable so that each user can maximize the modulation depth according to personal visual tolerance, thus achieving the best Alzheimer treatment for the individual. Another lighting apparatus includes a first light source, a second light source, and a controller. The controller turns on the first light source without strobing and the second light source with a strobing frequency between 35 Hz and 45 Hz. The controller regulates the light output of the second light source with a modulation depth less than the light output of the first light source.

16 Claims, 4 Drawing Sheets

Related U.S. Application Data which is a continuation-in-part of application No. 17/981,123, filed on Nov. 4, 2022, now Pat. No. 12,048,078, which is a continuation-in-part of application No. 17/509,877, filed on Oct. 25, 2021, now abandoned, which is a continuation-in-part of application No. 17/148,277, filed on Jan. 13, 2021, now Pat. No. 11,191,863, which is a continuation-in-part of application No. 17/094,567, filed on Nov. 10, 2020, now Pat. No. 11,103,612, which is a continuation-in-part of application No. 16/180,416, filed on Nov. 5, 2018, now Pat. No. 10,874,762.

(51) Int. Cl.
*H05B 45/10* (2020.01)
*H05B 45/20* (2020.01)

(58) Field of Classification Search
CPC ........... A61B 5/30; A61B 5/369; A61B 5/372; A61B 5/374; A61B 5/375; A61B 5/377; A61B 5/378; A61B 5/38; A61B 5/389; A61B 5/398; A61B 5/4094; A61B 5/486; A61B 5/6803; A61B 5/6814; A61B 5/6898; A61B 5/7207; A61M 2205/587; A61N 5/0618; A61N 5/0622; A61N 2005/0663; A61N 1/0456; A61N 1/36025; A61N 2005/0648; A61N 2005/0651; A61N 2005/0662; A61N 5/062; A61N 1/0404; A61N 1/0476; A61N 1/0492; A61N 1/36014; A61N 2/002; A61N 2/006; A61N 2/02; A61N 2005/0602; A61N 2005/0605; A61N 2005/0606; A61N 2005/0607; A61N 2005/0608; A61N 2005/061; A61N 2005/0611; A61N 2005/0612; A61N 2005/0626; A61N 2005/0627; A61N 2005/0629; A61N 2005/063; A61N 2005/0637; A61N 2005/0642; A61N 2005/0644; A61N 2005/0645; A61N 2005/0647; A61N 2005/0654; A61N 2005/0659; A61N 2005/0661; A61N 5/0603; A61N 5/0624
See application file for complete search history.

LIGHTING APPARATUS WITH INVISIBLE STROBING

BACKGROUND

The present disclosure is a continuation-in-part (CIP) of U.S. patent application Ser. No. 18/101,569, filed Jan. 25, 2023, which is a CIP of U.S. patent application Ser. No. 17/981,123, filed Nov. 4, 2022. Contents of aforementioned applications are herein incorporated by reference in their entirety.

TECHNICAL FIELD

The present disclosure pertains to the field of lighting apparatus and, more specifically, proposes a lighting apparatus with invisible strobing.

DESCRIPTION OF RELATED ART

It has been discovered that by flickering a light at a frequency between 35 to 45 Hz or generating a sound at a similar frequency has the effect of stimulating the cells in certain region of the brain, resulting in using a flicking light or a sound at such a frequency for treating Alzheimer's disease. However, turning on and off a light source at a frequency between 35 to 45 Hz can create visual discomfort to the eyes of a patient. Different approaches have been introduced to overcome this visual discomfort under 40 Hz flickering light. In U.S. patent application Ser. No. 17/981,123, the fusion of two light sources each with a distinct spectral power distribution was introduced for creating an invisible flickering light. However, the SPD fusion lighting apparatus introduced in U.S. patent application Ser. No. 17/981,123 is very strict in that the first visible light source and the second visible light source must have similar chromaticity coordinates on the CIE 1931 color space chromaticity diagram and at the same time they must have markedly different SPDs in a 50 nm wavelength range. Only custom-made LED light sources could meet these conditions, thus resulting in a higher production cost and subsequently a higher end user price. Later, in U.S. patent application Ser. No. 18/101,569, the fusion of two light sources each with a distinct color temperature was introduced for creating a fused color temperature with invisible flickering. While the teaching in U.S. patent application Ser. No. 18/101,569 does not require to use custom made LED light sources, it is still necessary to use two light sources each with a different color temperature and to have the controller to properly blend the intensity of the light output of these two light sources in order to create a target blended (fused) color temperature. The color temperature fusion when coupling with color tuning may complicate the design of the controller.

The present disclosure proposes a lighting apparatus using only one light source to strobe at a frequency between 35 to 45 Hz with a modulation depth percentage less than 50%. The present disclosure further proposes another lighting apparatus using two light sources with the same color temperature such that only one of the two light sources would strobe at a frequency between 35 to 45 Hz while the other doesn't. The design of the controllers of these two lighting apparatuses is thus simplified as compared to the design of the controller introduced in U.S. patent application Ser. No. 18/101,569.

SUMMARY

In one aspect, the lighting apparatus comprises a light source and a controller. The controller is configured to turn on the light source with strobing at a strobing frequency between 35 Hz and 45 Hz and to regulate the light output of the light source with a modulation depth percentage less than 50%. For example, if the maximum light output of the light source is 1000 lm, then the controller regulates the light output of the light source to strobe between 500 lm to 1000 lm. In practice, the modulation depth percentage may be lower than 50%, e.g., 20%, thus strobing between 800 lm and 1000 lm. The greater the modulation depth, the more effective the treatment is for an Alzheimer's patient. However, the downside is that with a greater modulation depth, the strobing may become more visible and may lead to visual discomfort for the patient. There are no restrictions on the form factor of the lighting apparatus. The lighting apparatus may be in the form of a luminaire or a portable electronic device such as smartphone, so long it has a light source and a controller configured to turn on the light source with strobing at a strobing frequency between 35 Hz and 45 Hz and to regulate the light output of the light source with a modulation depth percentage less than 50%.

In some embodiments, the controller is configured to strobe the light output of the light source according to a symmetric periodic wave form, e.g., a square wave form, a triangle wave form, a sinusoidal wave form, or another symmetric periodic wave form. FIG. 1(*a*) shows a strobing light output of the light source in a square wave form, FIG. 2(*b*) in a triangle wave form, and FIG. 3(*a*) in a sinusoidal wave form. The strobing light in a square wave form is most perceptible whereas the strobing light in a triangle or a sinusoidal wave form is lesser perceptible.

In some embodiments, the controller is configured to adjust the modulation depth percentage of the light output of the light source. In other words, the modulation depth is adjustable, thus allowing each user or patient to adjust the modulation depth based on personal preference and visual tolerance. As mentioned earlier, the greater the modulation depth, the more effective the treatment is for an Alzheimer's patient. However, the downside is that with a greater modulation depth, the strobing may become more visible and may lead to visual discomfort for the patient. Moreover, for elderly people with vision deterioration and prone to Alzheimer's disease, they are less visual sensitive and thus can and should be given a stronger visual strobing stimulation for treating their Alzheimer's disease more effectively. Therefore, it is preferrable to support an adjustable modulation depth such that for more visual sensitive people or for preventative Alzheimer treatment, the modulation depth percentage may be set to a lower level, e.g., 10%. For elderly people with Alzheimer's disease, the modulation depth percentage may be set to a higher level e.g., 30% or higher for a stronger visual stimulation and thus resulting in a more effective Alzheimer treatment.

In some embodiments, the controller is configured to dim the light output of the light source while maintaining the same modulation depth percentage. For example, if the maximum light output of the light source is 1000 lm and the modulation depth percentage to be 20%, the controller would strobe the light output of the light source between 800 lm and 1000 lm. When the light output is dimmed to 500 lm, then the controller would strobe the light output of the light source between 400 lm and 5000 lm, i.e., keeping the modulation depth percentage at 20%.

In some embodiments, the light source is configured to support more than one color temperature, and the controller is configured to tune the light source from one color temperature to another color temperature while maintaining the same modulation depth percentage. Though this would increase the design complexity of the controller, it is still manageable since there is only one light source the controller needs to deal with.

Sometimes it may be desirable to suspend the invisible strobing operation of the lighting apparatus. Therefore, in some embodiments, the controller is configured to support a non-strobing mode in which the controller is configured to turn on the light source without strobing.

In some embodiments, the light source comprises a light emitting diode (LED), since LED light source is suitable for being turned on/off at a high frequency and at different intensity easily.

In another aspect, the lighting apparatus comprises a first light source having a color temperature, a second light source having the same color temperature, and a controller. The controller is configured to turn on the first light source without strobing. Moreover, the controller is configured to turn on the second light source with strobing at a strobing frequency between 35 Hz and 45 Hz and regulate the light output of the second light source with a modulation depth less than the light output of the first light source. For example, the first light source has a maximum light output of 500 lm, and the second light source also has a maximum light output of 500 lm. The controller may regulate the modulation depth of the light output of the second light source to be 400 lm (i.e., between 100 to 500 lm), resulting in a combined light output (of the first and the second light sources) strobing between 600 lm and 1000 lm for the lighting apparatus for a maximal strobing stimulation. Or alternatively, the controller may regulate the modulation depth of the light output of the second light source to be 200 lm (i.e., between 300 lm to 500 lm), resulting in a combined light output strobing between 800 lm and 1000 lm for the lighting apparatus. There are no restrictions on the form factor of the lighting apparatus. The lighting apparatus may be in the form of a luminaire or a portable electronic device such as smartphone, so long it has two light sources and a controller configured to turn on the first light source without strobing and the second light source with strobing at a strobing frequency between 35 Hz and 45 Hz and to and regulate the light output of the second light source with a modulation depth less than the light output of the first light source.

In some embodiments, the controller is configured to strobe the light output of the second light source according to a symmetric periodic wave form, e.g., a square wave form, a triangle wave form, a sinusoidal wave form, or another symmetric periodic wave form. FIG. 1(c) shows the strobing light output of the second light source in a square wave form. When superimposed with a non-strobing light output of the first light source as shown in FIG. 1(b), it results in a combined light output for the lighting apparatus as shown in FIG. 1(a). Similarly, FIG. 2(c) shows the strobing light output of the second light source in a triangle wave form. When superimposed with a non-strobing light output of the first light source as shown in FIC. 2(b), it results in a combined light output for the lighting apparatus as shown in FIG. 2(a). FIG. 3(c) shows the strobing light output of the second light source in a sinusoidal wave form. When superimposed with a non-strobing light output of the first light source as shown in FIC. 2(b), it results in a combined light output for the lighting apparatus as shown in FIG. 1(a).

In some embodiments, the controller is configured to adjust the modulation depth of the light output of the second light source. In other words, the modulation depth is adjustable, thus each user or patient can adjust the modulation depth based on personal preference and visual tolerance.

In some embodiments, the controller is configured to dim the light outputs of the first light source and of the second light source simultaneously and proportionally. For example, the first light source has a maximum light output of 500 lm, and the second light source also has a maximum light output of 500 lm, and the controller regulate the modulation depth of the light output of the second light source between 300 lm to 500 lm, resulting in a combined light output strobing between 800 lm and 1000 lm for the lighting apparatus. When dimming is performed, say to 50%, the light output of the first light source drops to 250 lm, and the light output of the second light source strobes between 150 lm to 250 lm, resulting a strobing light output of 400 lm to 500 lm for the lighting apparatus.

In some embodiments, the first light source and the second light source are configured to support more than one color temperature, and the controller is configured to tune the first light source and the second light source from one color temperature to another color temperature simultaneously. In other words, the controller is configured to ensure that the first light source and the second light source always produce the same color temperature.

Sometimes it may be desirable to suspend the invisible strobing operation of the lighting apparatus. Therefore, in some embodiments, the controller is configured to support a non-strobing mode in which the controller is configured to turn on the second light source without strobing.

In some embodiments, the first light source comprises a first LED, and wherein the second light source comprises a second LED.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

The present disclosure discloses a lighting apparatus that includes a light source and a controller. The controller turns on the light source with a strobing frequency between 35 Hz and 45 Hz with a modulation depth percentage less than 50%. The present disclosure further discloses another lighting apparatus including a first light source, a second light source, and a controller. The controller turns on the first light source without strobing and the second light source with a strobing frequency between 35 Hz and 45 Hz. Moreover, the controller regulates the light output of the second light source with a modulation depth less than the light output of the first light source.

EXAMPLE IMPLEMENTATIONS

Figure 1:
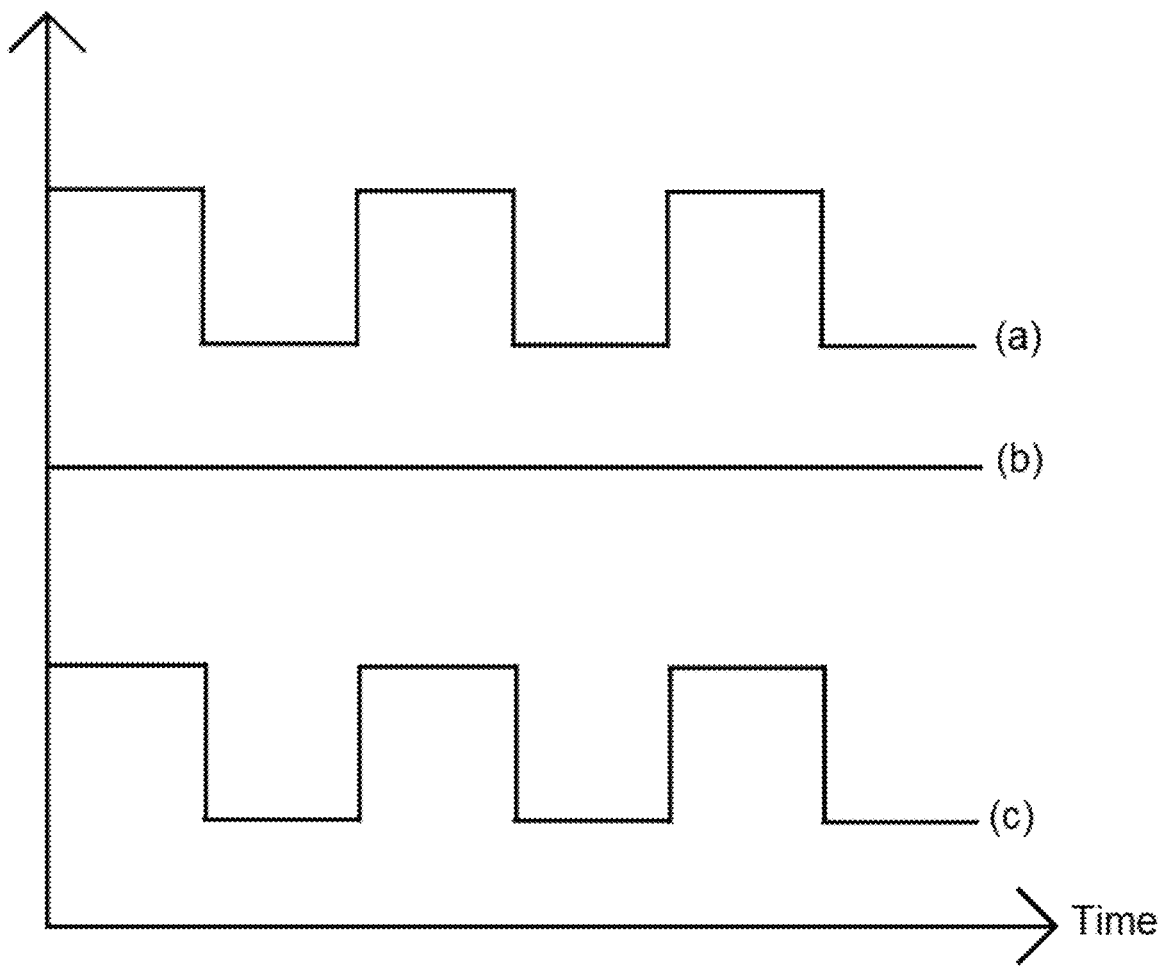
FIG. 1 schematically depicts a strobing light output in a square wave form.
Figure 2:
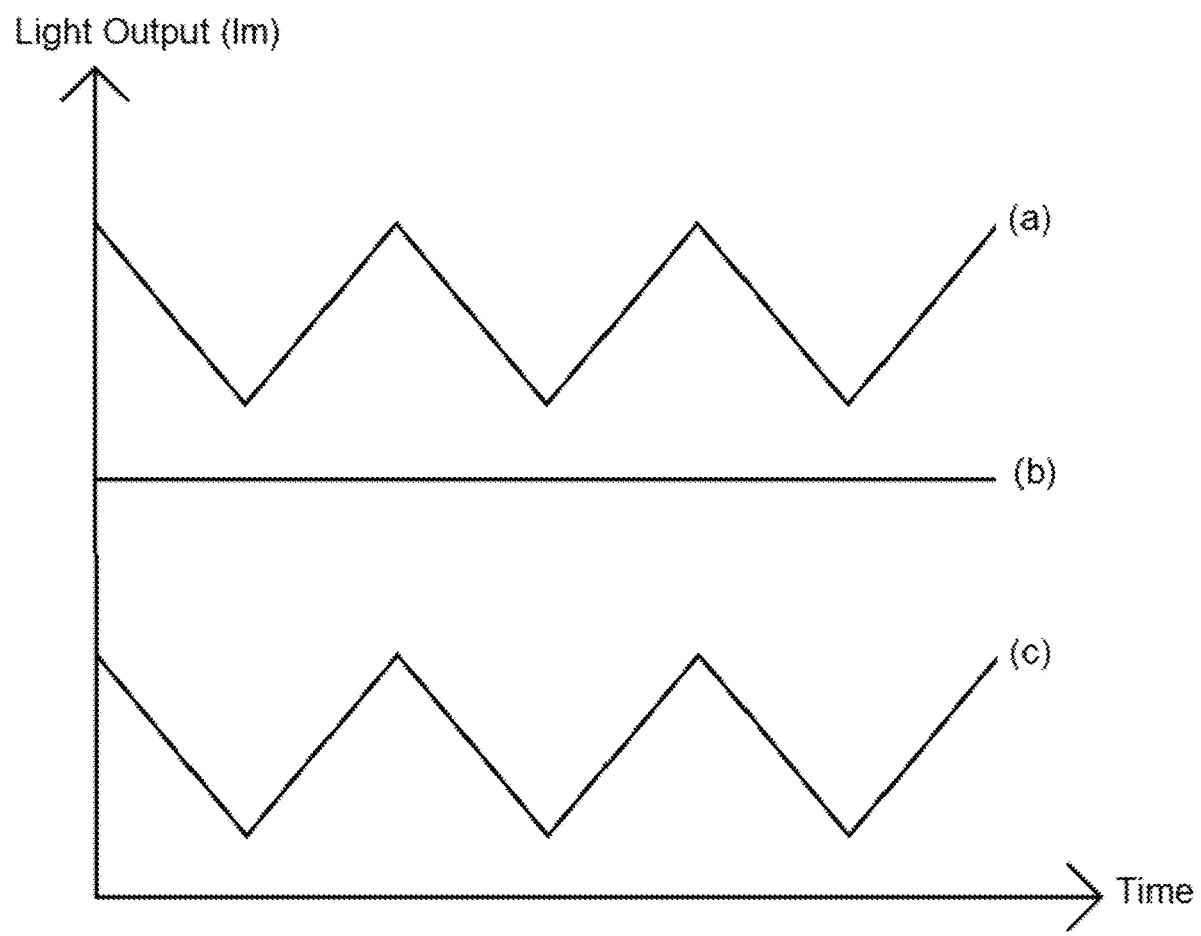
FIG. 2 schematically depicts a strobing light output in a triangle wave form.
Figure 3:
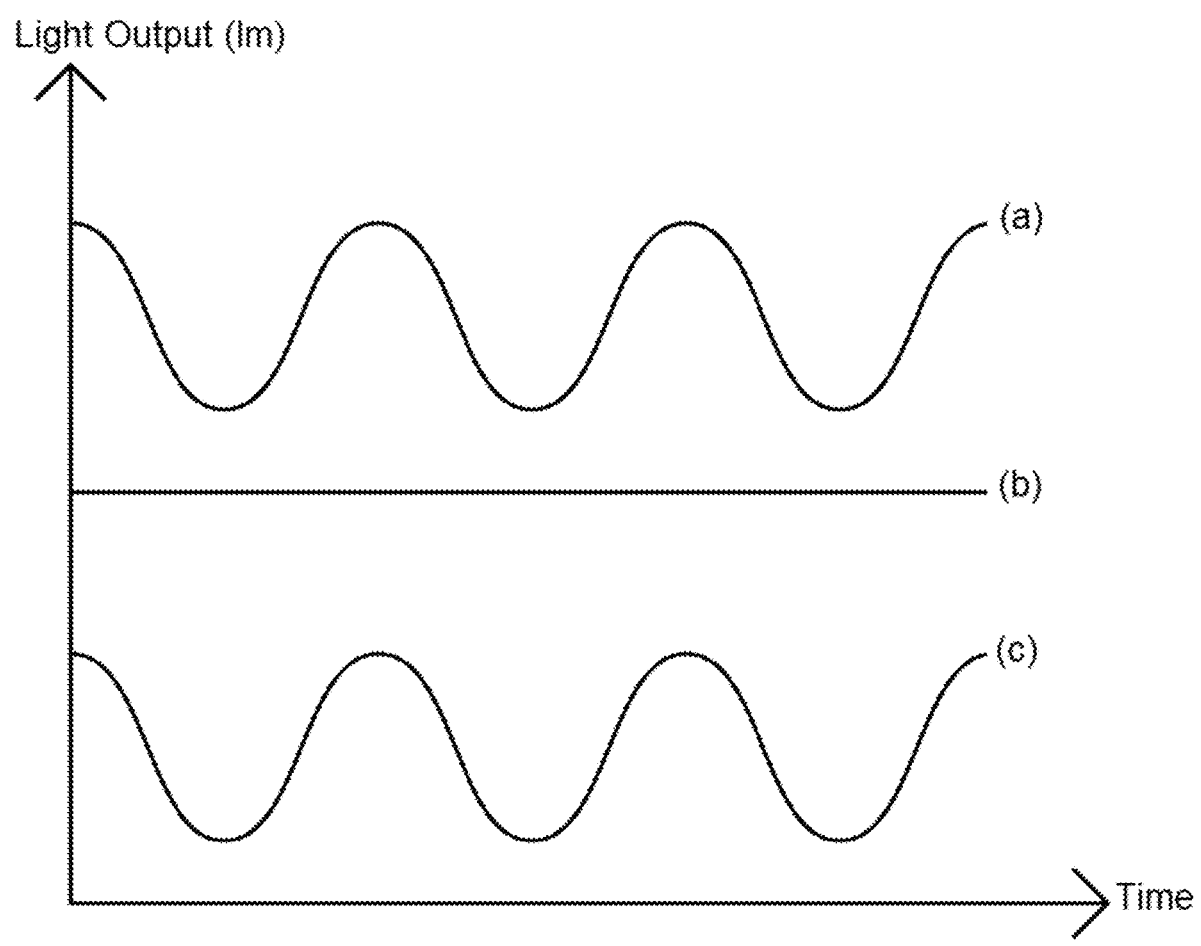
FIG. 3 schematically depicts a strobing light output in a sinusoidal wave form.
Figure 4:
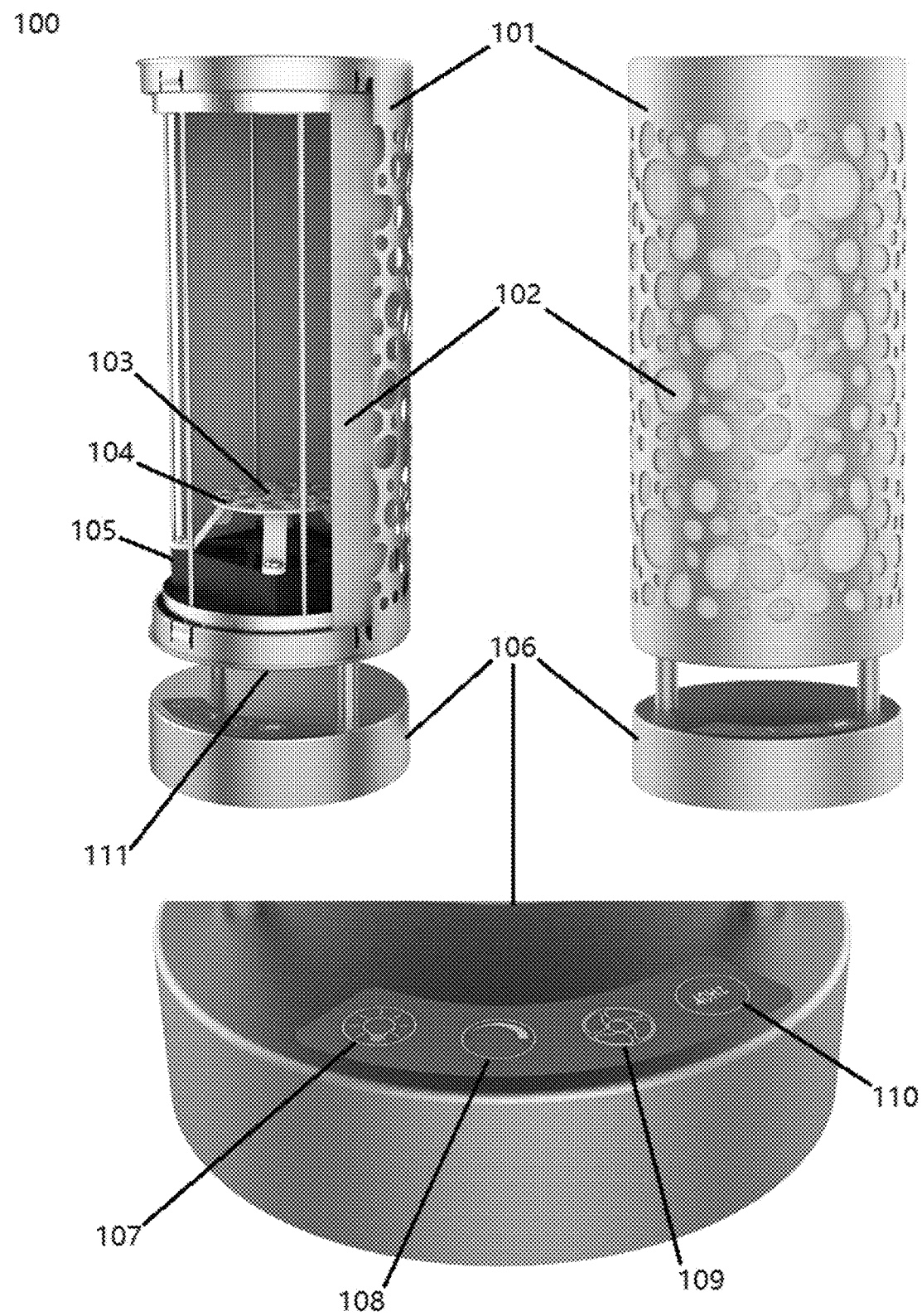
FIG. 4 schematically depicts an embodiment of the present disclosure in the form of a table lamp.

FIG. 1 is an embodiment of the therapeutic lighting device of the present disclosure in the form of a table lamp 100. The desktop lamp 100 has an external housing 101 to house an air filter 102, a fan 105, and two types of LEDs: 3000K white LEDs 104 and 5000K white LEDs 103. The controller is hidden inside the base 106 and is configured to provide various functions: color selection (via touch button 107), bi-level dimming (via touch button 108), fan operation 109 (via touch button 109), and 40 Hz strobing operation (via touch button 110).

The hidden controller is configured to supports via the touch button 107 three color temperatures: 3000K, 4000K, and 5000K, where 4000K color temperature is generated by turning on 3000K white LEDs 104 and 5000K white LEDs 103 at 50% of light intensity simultaneously. The hidden controller is configured to support via the touch button 108 two dimming levels: 50% and 100%.

There are two different approaches for the controller to support the 40 Hz strobing operation for the table lamp 100. Under a first approach, the controller is configured to strobe both 3000K white LEDs 104 and 5000K white LEDs 103 at 40 Hz with a square wave form and with a modulation depth percentage set to, say, 20%. During the strobing operation, a user can still change the color temperature of the table lamp via the touch button 107. The controller is configured to maintain the same modulation depth percentage on 3000K white LEDs 104 and 5000K white LEDs 103 regardless the color temperature. Similarly, the controller is configured to maintain the same modulation depth percentage on 3000K white LEDs 104 and 5000K white LEDs 103 whether the dimming level is 50% or 100%.

Under a second approach for the 40 Hz strobing operation, the first light source comprises 80% of 3000 K white LEDs 104 and 80% of 5000K white LEDs 103, which will be turned on by the controller without strobing. The second light source comprises the remaining 20% of 3000K white LEDs 104 and the remaining 20% of 5000K white LEDs 103, which will be regulated by the controller to strobe with 100% modulation depth in a square form. Since only 20% of the LEDs (104 and 103) will strobe 100% modulation depth, the overall light output of the table lamp 100 will have a modulation depth percentage at 20%, i.e., equivalent to the first approach of implementing the 40 Hz strobing operation.

Though not shown, another touch button may be added for the controller to support the adjustment of the modulation depth percentage such that the modulation depth may be adjusted from, say, 5% to 40% according to a user's personal preference.

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting apparatus, comprising:
   a light source; and
   a controller,
   wherein:
      the controller is configured to turn on the light source with strobing at a strobing frequency between 35 Hz and 45 Hz and to regulate a light output of the light source with a modulation depth percentage less than 50%.

2. The lighting apparatus of claim 1, wherein the controller is configured to strobe the light output of the light source according to a symmetric periodic wave form.

3. The lighting apparatus of claim 2, wherein the symmetric periodic wave form comprises a square wave form, a triangle wave form, a sinusoidal wave form, or another symmetric periodic wave form.

4. The lighting apparatus of claim 1, wherein the controller is configured to adjust the modulation depth percentage of the light output of the light source.

5. The lighting apparatus of claim 1, wherein the controller is configured to dim the light output of the light source while maintaining a same modulation depth percentage.

6. The lighting apparatus of claim 1, wherein the light source is configured to support more than one color temperature, and wherein the controller is configured to tune the light source from one color temperature to another color temperature while maintaining a same modulation depth percentage.

7. The lighting apparatus of claim 1, wherein the controller is configured to support a non-strobing mode in which the controller turns on the light source without strobing.

8. The lighting apparatus of claim 1, wherein the light source comprises a light emitting diode (LED).

9. A lighting apparatus, comprising:
   a controller;
   a first light source having a color temperature; and
   a second light source having a same color temperature as that of the first light source,
   wherein:
      the controller is configured to turn on the first light source without strobing, and
      the controller is configured to turn on the second light source with strobing at a strobing frequency between 35 Hz and 45 Hz and to regulate a light output of the second light source with a modulation depth less than a light output of the first light source.

10. The lighting apparatus of claim 9, wherein the controller is configured to strobe the light output of the second light source according to a symmetric periodic wave form.

11. The lighting apparatus of claim 10, wherein the symmetric periodic wave form comprises a square wave form, a triangle wave form, a sinusoidal wave form, or another symmetric periodic wave form.

12. The lighting apparatus of claim 9, wherein the controller is configured to adjust the modulation depth of the light output of the second light source.

13. The lighting apparatus of claim 9, wherein the controller is configured to dim the light outputs of the first light source and the light output of the second light source simultaneously and proportionally.

14. The lighting apparatus of claim 9, wherein the first light source and the second light source are configured to support more than one color temperature, and wherein the controller is configured to tune the first light source and the second light source from one color temperature to another color temperature simultaneously.

15. The lighting apparatus of claim 9, wherein the controller is configured to support a non-strobing mode in which the controller turns on the second light source without strobing.

16. The lighting apparatus of claim 9, wherein the first light source comprises a first light emitting diode (LED), and wherein the second light source comprises a second LED.

\* \* \* \* \*